United States Patent
Arnold et al.

(12) 
(10) Patent No.: US 6,410,231 B1
(45) Date of Patent: Jun. 25, 2002

(54) SNP DETECTION

(75) Inventors: Lyle Arnold, Paway; Thomas Theriault, Manhattan Beach; Tod Bedilion, San Carlos, all of CA (US)

(73) Assignee: Incyte Genomics, Inc., Palo Alto, CA (US)

( * ) Notice: Subject to any disclaimer, the term of this patent is extended or adjusted under 35 U.S.C. 154(b) by 0 days.

(21) Appl. No.: 09/259,898

(22) Filed: Feb. 26, 1999

(51) Int. Cl.[7] .................... C12Q 1/68; C12P 19/34; C07H 21/04

(52) U.S. Cl. ................ 435/6; 435/91.1; 536/23.1; 536/24.3

(58) Field of Search ................ 435/6, 91.1, 91.2; 536/23.1, 24.3; 514/44

(56) References Cited

U.S. PATENT DOCUMENTS

| | | | | |
|---|---|---|---|---|
| 5,627,032 A | * | 5/1997 | Ulanovsky | 435/6 |
| 5,633,134 A | * | 5/1997 | Shuber | 435/6 |
| 5,700,637 A | * | 12/1997 | Southern | 435/6 |
| 5,801,155 A | * | 9/1998 | Kutyavin et al. | 514/44 |
| 5,830,645 A | * | 11/1998 | Pinkel et al. | 435/6 |
| 5,976,798 A | * | 11/1999 | Parker et al. | 435/6 |
| 6,017,696 A | * | 1/2000 | Heller | 435/6 |
| 6,051,379 A | * | 4/2000 | Lescallet et al. | 435/6 |

FOREIGN PATENT DOCUMENTS

| WO | 96/31622 | 10/1996 |
|---|---|---|

* cited by examiner

*Primary Examiner*—W. Gary Jones
*Assistant Examiner*—Jehanne Souaya
(74) *Attorney, Agent, or Firm*—Richard Aron Osman

(57) ABSTRACT

The invention provides methods, compositions and systems for detecting multiple single nucleotide polymorphisms (SNPs) in a population of target polynucleotides in parallel in a sandwich assay employing SNP probes, capture polynucleotides and, optionally, auxiliary polynucleotides. The relative affinities of the SNP probes for the corresponding SNP regions can be increased with reagents which normalize the melting temperatures of the probes and/or by positionally facilitating interactions between the SNP probe, the SNP region, the capture polynucleotide and/or the auxiliary polynucleotides, such as through a minor groove binder. The probes may comprise a degenerate set of all possible same-sized polynucleotides and the capture polynucleotides are generally immobilized and arrayed at corresponding discrete elements in high density.

20 Claims, 4 Drawing Sheets

SNP DETECTION

FIELD OF THE INVENTION

The invention is in the field of genetic analysis (genotyping).

BACKGROUND

The ability to detect variations in nucleic acid sequences is of great importance in the field of medical genetics: the detection of genetic variation is essential, inter alia, for identifying polymorphisms for genetic studies, to determine the molecular basis of inherited diseases, to provide carrier and prenatal diagnosis for genetic counseling and to facilitate individualized medicine. Detection and analysis of genetic variation at the DNA level has been performed by karyotyping, analysis of restriction fragment length polymorphisms (RFLPs) or variable nucleotide type polymorphisms (VNTRs), and more recently, analysis of single nucleotide polymorphisms (SNPs), see e.g. Lai E, et al., Genomics, 1998, 15;54(1):31–8; Gu Z, et al., Hum Mutat.1998;12(4):221–5; Taillon-Miller P, et al., Genome Res. 1998;8(7):748–54; Weiss K M., Genome Res. 1998;8 (7):691–7; Zhao L P, et al., Am J Hum Genet. 1998; 63(1):225–40.

A wide variety of techniques have been developed for SNP detection and analysis, see, e.g. Sapolsky et al. (1999) U.S. Pat. No. 5,858,659; Shuber (1997) U.S. Pat. No. 5,633,134; Dahlberg (1998) U.S. Pat. No. 5,719,028; Murigneux (1998) WO98/30717; Shuber (1997) WO97/10366; Murphy et al. (1998) WO98/44157; Lander et al. (1998) WO98/20165; Goelet et al. (1995) WO95/12607 and Cronin et al. (1998) WO98/30883. In addition, ligase based methods are described by Barany et al. (1997) WO97/31256 and Chen et al. Genome Res. 1998;8(5):549–56; mass-spectroscopy-based methods by Monforte (1998) WO98/12355, Turano et al. (1998) WO98/14616 and Ross et al. (1997) Anal Chem. 15, 4197–202; PCR-based methods by Hauser, et al. (1998) Plant J. 16,117–25; exonuclease-based methods by Mundy U.S. Pat. No. 4,656,127; dideoxynucleotide-based methods by Cohen et al. WO91/02087; Genetic Bit Analysis or GBA™ by Goelet et al. WO92/15712; Oligonucleotide Ligation Assays or OLAs by Landegren et al.(1988) Science 241:1077–1080 and Nickerson et al.(1990) Proc. Natl. Acad. Sci. (U.S.A.) 87:8923–8927; and primer-guided nucleotide incorporation procedures by Prezant et al.(1992) Hum. Mutat. 1:159–164; Ugozzoli et al.(1992) GATA 9:107–112; Nyréen et al. (1993) Anal. Biochem. 208:171–175.

SUMMARY OF THE INVENTION

The invention provides methods, compositions and systems for detecting multiple SNPs in a population of target polynucleotides in parallel. In general, the methods comprise the steps of: (a) combining target polynucleotides, capture polynucleotides and SNP probes under conditions wherein: each target polynucleotide comprises a different capture region and a different SNP region comprising a corresponding different SNP, the capture polynucleotides are immobilized and arrayed at corresponding discrete elements on a substrate and each capture polynucleotide comprises a sequence which specifically hybridizes to a corresponding different capture region, each SNP probe comprises a sequence complementary to a corresponding SNP region, the target polynucleotides are immobilized by hybridizing to the capture polynucleotides whereby each target polynucleotide is immobilized at a corresponding discrete element of the substrate, and the relative affinity of each SNP probe for the corresponding SNP region is sufficient to provide selective hybridization of the SNP probe to the corresponding SNP region, whereby each SNP probe hybridizes to the corresponding SNP region; and (b) detecting the presence of each SNP probe on the substrate, wherein the presence of a given SNP probe at a given element indicates the presence of the corresponding SNP in the corresponding target polynucleotide.

In a particular embodiment, the relative affinity of each SNP probe for the corresponding SNP region is increased sufficiently to provide enhanced selective hybridization of the SNP probe to the corresponding SNP region, whereby each SNP probe hybridizes to the corresponding SNP region; and (b) detecting the presence of each SNP probe on the substrate, wherein the presence of a given SNP probe at a given element indicates the presence of the corresponding SNP in the corresponding target polynucleotide.

In particular embodiments, the SNP probes are a subset of assay probes and the relative affinity of each SNP probe for the corresponding SNP region is increased at least in part by at least one of: (a) a method comprising the step of including in the combining step a reagent which normalizes the melting temperatures of the assay probes and (b) the SNP probe interacting with the capture polynucleotide or an auxiliary probe hybridized to the corresponding target polynucleotide, e.g. through a minor groove binder tethered to at least one of the SNP probe, the capture polynucleotide and the auxiliary probe.

In other embodiments of the general method, the assay probes comprise a degenerate set of all possible same-sized polynucleotides; the target polynucleotides are a subset of sample polynucleotides and the sample polynucleotides comprise fragmented genomic DNA; the capture polynucleotides are a subset of immobilized polynucleotides and the immobilized polynucleotides are a segregated and arrayed cDNA library; the capture polynucleotides are immobilized and arrayed at corresponding discrete elements in high density; and/or each SNP probe comprises a label.

The subject compositions include reagent sets and/or mixtures suited to the disclosed methods and the subject systems may further comprise kits and/or equipment suited to the disclosed methods.

DETAILED DESCRIPTION OF PARTICULAR EMBODIMENTS OF THE INVENTION

Figure 1:
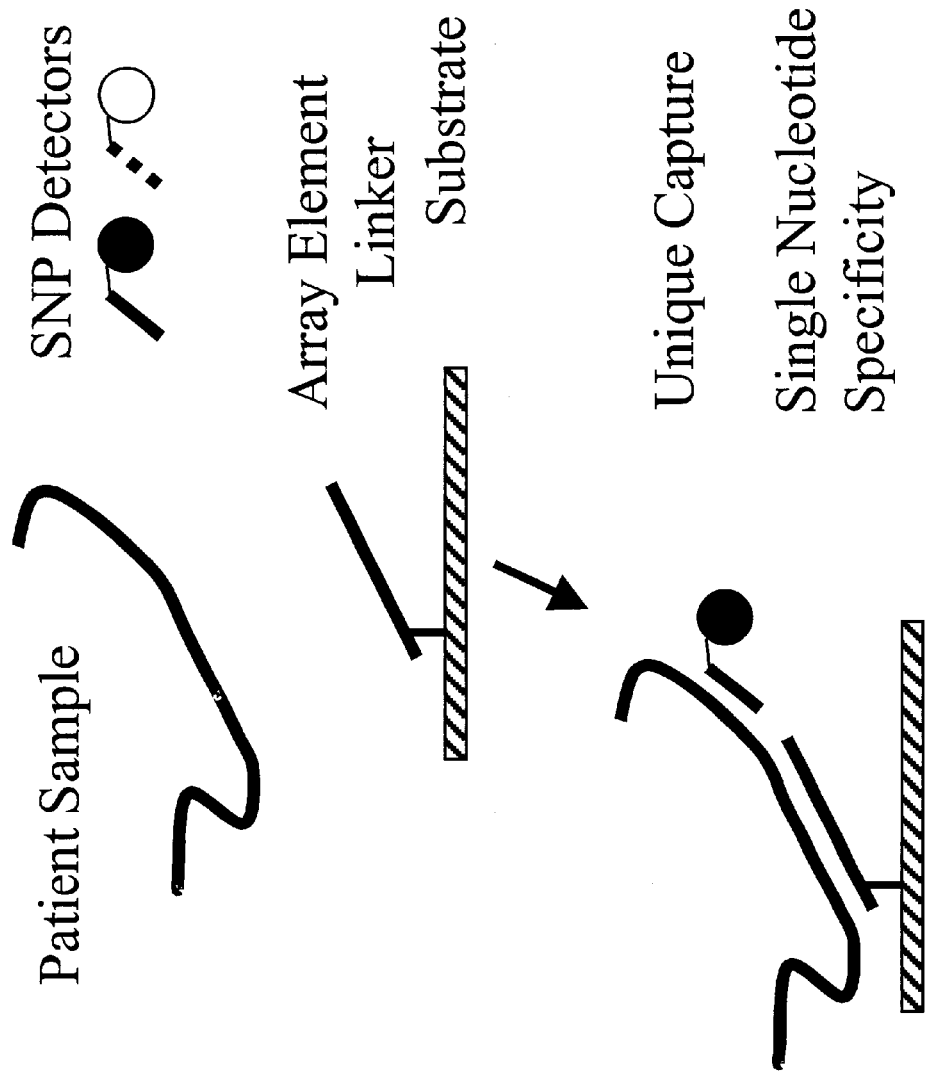
FIG. 1 shows a schematic of SNP detection using a support-bound capture polynucleotide and labeled SNP detector polynucleotides.
Figure 2:
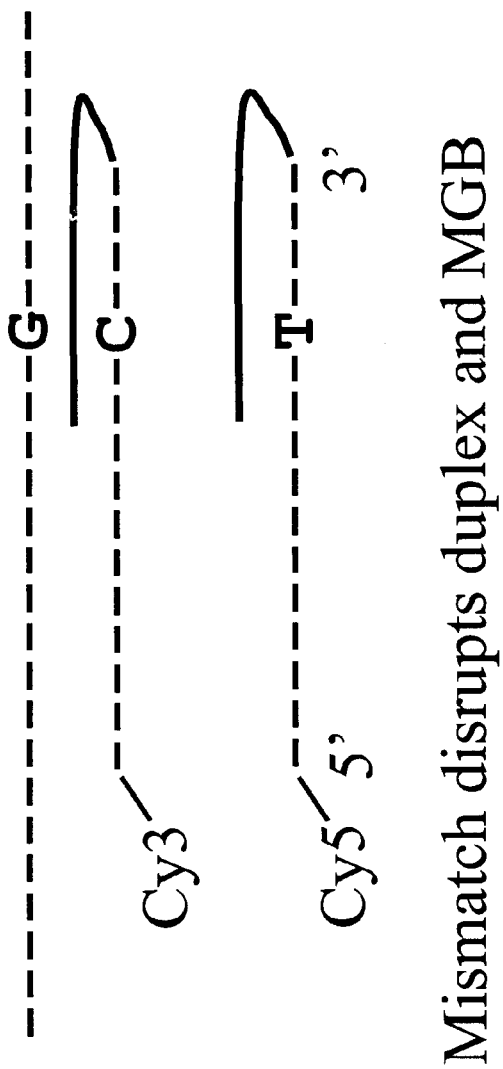
FIG. 2 shows a schematic of SNP detection using a support-bound capture polynucleotide and labeled SNP detector polynucleotides tethered to an MGB.

The following descriptions of particular embodiments and examples are offered by way of illustration and not by way of limitation.

Unless contraindicated or noted otherwise, throughout this specification, the terms "a" and "an" mean one or more, and the term "or" means and/or.

The first step of the general method involves combining or forming a mixture of target polynucleotides, capture polynucleotides and SNP probes. These constituents each comprise a polynucleotide sequence, i.e. a polymer of nucleotides or analogs thereof. The length and sequence of the polynucleotides vary depending on their type and application. For example, target polynucleotides are often measured in kilobases, while probe polynucleotides may be no more than a few nucleotides in length. The bases of the polynucleotides will generally be A, T (or U), C or G, but may also or alternatively comprise functional equivalents thereof which will pair bond the complementary base or functional equivalent thereof in double and/or triple stranded polynucleotides. Such functional equivalents are known in the art and include 1,2 diamino purine, inosine, methylated nucleobases, etc. Similarly, the sugar, molecular backbone and internucleotide bonds will generally be natural components (e.g. ribose or deoxyribose sugars coupled through phosphodiester bonds) but may also or alternatively include functional equivalents thereof providing similar or analogous functionality. Such equivalents are known in the art and include peptide nucleic acids (PNAs), phosphorothioates, sugar modifications such as 2' O-alkyl sugars, base analogs such as comprising deaza-modifications, thioguanine, etc. Other variables of the polynucleotides employed in the methods, such as length, strandedness, GC content, secondary structure, etc., are readily selected for optimal performance under assay conditions, as described and exemplified below for each polynucleotide.

The target polynucleotides of the method each comprise a different capture region and a different SNP region comprising a corresponding different SNP. Functionally, these are the regions that hybridize with the capture polynucleotide and the SNP probe, respectively. The capture and SNP regions may be fully or partly overlapping and require invasion of capture region—capture polynucleotide hybrids by the SNP probe (e.g. triple helix formation) or may be non-overlapping (i.e. positionally distinct). Generally, the target polynucleotides (those molecules that are actually immobilized and assayed for SNP probe binding in the method) are a subset of sample polynucleotides. The sample polynucleotides may be derived from any source sought to be analyzed for SNPs, using well-established techniques, including genomic fragmented DNA, random amplified genomic DNA, PCR amplified DNA, RNA, cDNA, etc. In a particular embodiment, the sample polynucleotides comprise fragmented genomic DNA from a human tissue. For example, DNA can be obtained from: (i) blood leukocytes obtained from whole blood; (ii) buccal cells obtained using a swab or cytobrush or using a mouthwash technique (Lench, N. et. al. *The Lancet* 1:1356–8 (Jun. 18, 1988,)); (iii) cervicovaginal cells obtained using a brush, swab or lavage (Burk, R. D. and C. Spitzer *Am J Obstet Gynecol.* 162:6524 (1990); (iv) epithelial cells obtained from urine (Gasparini, P. et. al. *N. Engl. J. Med* 320:809 (1989) or hair roots (Higuchi, R. et. al. *Nature* 332:543–6 (1988); (v) fetal cells obtained from amniotic fluid, cord blood, chorionic villus tissue, cervical secretions or maternal blood (Bianchi, D. W. et. al *Proc. Natl. Acad. Sci. USA* 87:3279–83 (1990); (vi) embryonic cells obtained from biopsied embryos, etc. Once obtained, sample polynucleotides can be prepared for hybridization using techniques that are well-known in the art. For example, a wide variety of established polynucleotide amplification procedures may be used to increase the number of polynucleotides available for hybridization and thereby the ultimate signal obtained in the disclosed methods.

The capture polynucleotides of the invention comprise a sequence of length and sufficient complementarity to a corresponding different capture region to specifically hybridize with that capture region under the conditions of the combining step. Generally, the capture polynucleotides (those molecules that retain target polynucleotides) are a subset of immobilized polynucleotides. The immobilized polynucleotides may be derived from a wide variety of sources, including amplified and/or cloned DNA fragments, cDNA, etc, using well-established techniques. In a particular embodiment, the immobilized polynucleotides effect a reduction in complexity of the sample polynucleotides by retaining by hybridization only a functional, preferably a predetermined functional subset thereof. For example, a segregated and arrayed cDNA library may be used as immobilized polynucleotides to select a subset (reduce the complexity) of fragmented genomic DNA sample polynucleotides. Before, during or after such hybridization (the hybridization may occur in solution or in solid phase), the capture polynucleotides are immobilized and arrayed at corresponding discrete, non-overlapping elements on a substrate, such that each element contains a different capture polynucleotide. A wide variety of materials and methods are known in the art for arraying polynucleotides at discrete elements of substrates such as glass, silicon, plastics, nylon membranes, etc., including contact deposition, e.g. U.S. Pat. Nos. 5,807,522; 5,770,151, etc.; photolithography-based methods, e.g. U.S. Pat. Nos. 5,861,242; 5,858,659; 5,856,174; 5,856,101; 5,837,832, etc; flow path-based methods, e.g. U.S. Pat. No. 5,384,261; dip-pen nanolithography-based methods, e.g. Piner, et al., Science Jan. 29, 1999: 661–663, etc.; etc. In a preferred embodiment, the capture polynucleotides are arrayed at corresponding discrete elements in high density, generally at least 100, preferably at least 1000, more preferably at least 10,000, most preferably at least 100,000 discrete elements per square centimeter.

The SNP probes of the invention are polynucleotides comprising a sequence of sufficient complementarity to a corresponding SNP region to specifically hybridize with that SNP region under the conditions of the combining step. Generally, the SNP probes (those molecules that are retained by hybridization to target polynucleotides) are a subset of assay probes, which are typically designed to be allele-specific, selectively hybridizing with a targeted allele in the presence of one or more different, polymorphic forms of the allele, providing a binary signal. The polymorphic site of each probe is generally flanked on both sides by regions common to the different alleles.

Probes can be labeled with a directly or indirectly detectable marker according to procedures which are well known in the art, including radioactively end-labeling (e.g. using $^{32}P$ or $^{35}S$) and preferably, non-isotopic methods such as via direct or indirect attachment of mass spectroscopy labels, fluorochromes or enzymes, or by various chemical modifications of the nucleic acid fragments that render them detectable immunochemically or by other affinity reactions. For fluorometric labels, the method typically uses light input near the excitation maximum and collects near the emission maximum (plus or minus about 10 nanometers is acceptable in most cases). With lasers, excitation can occur far from the excitation maximum. In a particular embodiment, the invention exploits energy transfer dye multiples. For example, donor and acceptor moieties may be coupled to the same molecule (e.g. SNP probe) or to different molecules (e.g. the capture or target polynucleotide and the SNP probe, or one acceptor on the capture or target polynucleotide and two different acceptors on two different SNP probes), etc. Exemplary fluorescent labels and donor/acceptor pairs with their absorption and emission maxima are shown in Tables 1 and 2.

TABLE 1

Representative fluorescent label and absorption and emission maxima.

| Dye | Absorption Maximum (nm) | Emission Maximum (nm) |
|---|---|---|
| Cy2 | 489 | 506 |
| Cy3 | 550 | 570 |
| Cy3.5 | 581 | 596 |
| Cy5 | 649 | 670 |
| Cy7 | 743 | 767 |
| Fluorescein | 494 | 520 |
| Tetramethylrhodamine (mixed isomer) | 540 | 565 |
| Lissamine rhodamine B | 568 | 583 |
| Carboxyrhodamine 6G (mixed isomer) | 524 | 552 |
| Carboxy-X-rhodamine | 568 | 595 |
| Texas Red | 587 | 602 |

TABLE 2

Representative fluorescent label donor/acceptor pairs and absorption and emission maxima.

| Dye 1 | Abs. | Em. | Dye 2 | Abs. | Em. |
|---|---|---|---|---|---|
| Cy3 | 550 | 570 | Cy5 | 649 | 670 |
| Fluorescein | 494 | 520 | Lissamine | 568 | 583 |
| Carboxyrhodamine 6G | 524 | 552 | Texas Red | 587 | 602 |

To detect in a single reaction at a single array element multiple SNPs or a SNP with more than two alleles it is useful to provide multiple differentially detectable labels. For example, simultaneously probing for n (e.g. four) different alleles at a position exploits n (e.g. four) differentially detectable labels (e.g. Cy2, Cy3, Cy5 and Cy7), or simultaneously probing n different SNPs on a target with m alleles each exploits n×m differentially detectable labels (e.g. for two SNPs each with two alleles, this embodiment exploits four differentially detectable labels, measured as, for instance, a Cy2/Cy7 ration for one SNP and a Cy3/Cy5 for the second SNP). An analogous strategy is used to simultaneously probe the same SNP in a mixture of multiple samples at the same array spot.

Several probe parameters may be modulated to optimize signal strength and specificity. While probes used in a pool to detect multiple mutations in the same hybridization reaction are preferably of approximately the same length (i.e. approximately the same number of base pairs) and are of lengths readily synthesized using automated synthesizers, the length of the probes can be optimized for signal and allele discrimination. Probes that yield low signals can be lengthened while probes that show poor discrimination can be shortened. Suitable concentrations of a particular probe to be used in a pool are determined empirically. If the signal produced was too low, the concentration was doubled until the appropriate signal intensity was obtained, while minimizing background noise. For example, the optimal concentrations of each probe used in a pool to probe the cystic fibrosis transmembrane regulator gene, were initially tested at a concentration of 0.03 pmol. Other parameters to optimize signals include probe backbone and nucleotide alterations and temperature ramping to address different conditions for each SNP probe pair.

In a particular embodiment, the assay probes comprise a degenerate set of all possible polynucleotides that cover a defined sequence space, for example, all possible same-sized polynucleotides, e.g. those that are five nucleotides in length. This format provides in essence, a universal detector set. For example, the sub-population of such a set having an adenine nucleotide at a specific location, say the third position from the 3' end are labeled with a first label, those with a thymidine nucleotide are labeled with a second label, those with a quanine nucleotide are labeled with a third label, and those with a cytidine nucleotide are labeled with a forth label. With this collection of labeled degenerate SNP probes, the exact nucleotide type or combination of nucleotide types can be determined at a specific single location based on the label associated with the hybrid formed by specific target polynucleotide sequences and specific capture probes.

The combining step of the method involves increasing the relative affinity of each SNP probe for the corresponding SNP region sufficiently to provide selective hybridization of the SNP probe to the corresponding SNP region, or, decreasing the relative affinity of the probe to non-corresponding SNP regions or of one or more mismatched probes to the targeted SNP region. In aggregate, the increase in relative affinity is generally measured as an increase in the ratio of the binding of perfectly matched probe to the targeted SNP versus the binding of one or more mismatched probes (e.g. single base mismatched probes) binding to the targeted SNP, generally at least a 2 fold increase, preferably at least a 5 fold increase, more preferably at least a ten fold increase.

A wide variety of methods or assay conditions may be used to increase the relative affinity of each SNP probe for the corresponding SNP region. In one particular embodiment, the relative affinity of each SNP probe for the corresponding SNP region is increased at least in part by a method comprising the step of including in the combining step a reagent which normalizes the melting temperatures of the hybrids formed with the assay probes, in particular, normalizing the melting temperatures of the hybrids formed between the target SNP regions and SNP probes sufficient to provide discrimination between the corresponding SNP region and other than corresponding SNP regions, particularly other SNP regions, more particularly the SNP regions of alternative alleles of the corresponding SNP region. When using SNP probe pairs, this embodiment narrows the detected distribution of ratios of matched to mismatched probe binding. A wide variety of suitable normalizing reagents, including detergents (e.g. sodium dodecyl sulfate, Tween), denaturants (e.g. guanidine, quaternary ammonium salts), polycations (e.g. polylysine, spermine), minor groove binders (e.g. distamycin, CC-1065, see Kutyavin, et al., 1998, U.S. Pat. No. 5,801,155) , etc. and their use are described herein and/or otherwise known in the art. Effective concentrations and suitable assay conditions are readily determined empirically (see, e.g. Examples, below). In a particular embodiment, the denaturant is a quaternary ammonium salt such as tetramethyl ammonium chloride, tetraethyl ammonium chloride, tetramethyl ammonium fluoride or tetraethyl ammonium fluoride. Normalization may be confirmed by any convenient means, such as a reduction in the coefficient of variance (CV) or standard deviation, a reduction of at least 20%, preferably at least 40%, more preferably at least 60%, most preferably at least 80%). An increase in the ratio between the signal of a perfect match and for a single base mismatch indicates that a less stringent CV is required. For example, a ratio of 5:1 match to mismatch, CVs of 20% or lower are preferred, more preferably 10% or lower, while for a ratio of 50:1 match to mismatch, CVs of 50% or lower are preferred.

In another particular embodiment, the relative affinity of each SNP probe for the corresponding SNP region is increased at least in part by the SNP probe interacting with the capture polynucleotide or an auxiliary probe hybridized to the corresponding target polynucleotide. In other words, the SNP probes, capture polynucleotides, and/or auxiliary probes are constructed to form one or more cooperative interactions such that the SNP probe preferentially binds at only a single highly specific cooperative domain formed by hybridization of the target polynucleotide with the capture polynucleotide and/or auxiliary probe. The auxiliary probe may be any polynucleotide which hybridizes with the target polynucleotide and directly or indirectly increases the relative affinity of the corresponding SNP to the corresponding SNP region. Hence, the auxiliary probe hybridizes sufficiently proximate to the SNP region to provide such direct or indirect interaction. A wide variety of direct and indirect cooperative interactions are known in the art to enhance molecular binding affinity and/or stability, including charge-charge interactions, hydrophobic interactions, ring and/or pi-bond stacking, hybridization, triple strand formation, stearic cooperativity, minor groove or major groove binding interactions, etc. In a particular embodiment, minor groove binding moieties are attached to the end of the SNP probe in a conformation to enable the minor groove binders to associate with the minor groove formed by the hybridization of a capture polynucleotide and a specific target polynucleotide. Preferably, hybridization conditions are utilized that permit only a single perfectly matched SNP probe to bind to the cooperative domain In a particular embodiment, a minor groove binder (MGB) is tethered (e.g. through a molecular linker) to at least one of the SNP probe, the capture polynucleotide and the auxiliary probe wherein the MGB interacts with and stabilizes the capture-target and/or the target-probe (e.g. SNP probe) hybrids. Suitable minor groove binders include netropsin, distamycin and CC-1065. In addition, the minor groove binders enable melting temperature equalization between different probes sequences.

In a particular embodiment, the relative affinity of each SNP probe for the corresponding SNP region is increased at least in part by the SNP probe interacting with the capture polynucleotide or an auxiliary probe hybridized to the corresponding target polynucleotide and a method comprising the step of including in the combining step a reagent which normalizes the melting temperatures of the assay probes.

In a particular embodiment, following SNP probe hybridization, the method employs one or more wash or dilution steps which substantially separate from the substrate assay probes which do not selectively hybridize to immobilized sample polynucleotides. In order to increase the signal to noise ratio, hybridization and washes should be carried out under stringent conditions. In other words, the temperature at which the hybridization reaction is conducted should be as high as possible for the length of probe being used. The optimal stringency for a particular probe pool is determined empirically. As an example, for the 17 base pair probes used to probe the cystic fibrosis transmembrane regulator gene, hybridizations were carried out at 52° C. In addition, signal to noise ratios of hybridized mutation specific probes can be increased by including cold (i.e. non-labeled), normal (i.e. wild-type) probes or portions thereof to the hybridization reaction preferably in a concentration in the range of about 1 to 100 times the concentration of labeled probe.

Ultimately, the presence or absence of each SNP probe on the substrate is detected by conventional means appropriate for the particular label used. For example, if SNP probes are labeled with a fluorescent dye, hybridization can be detected using standard fluorimetry.

The methods are readily applied to large numbers of samples simultaneously for multiple mutations within a gene. In addition, they can be used to analyze simultaneously multiple different individuals having different. disease indications (e.g. cystic fibrosis, sickle cell anemia, β-thallasemia, Tay-Sachs, Gaucher's disease and cancers resulting from certain mutations in genes, such as the P-53 gene) in a single hybridization assay and yet achieve disease specific results.

EXAMPLES

Example 1

Sandwich Assay

A sandwich assay was designed to identify the A to G base substitution known to occur at the polymorphic site 858 of the apolipoprotein E (ApoE) gene. A 59-mer capture polynucleotide was synthesized to cover the region from nucleotides 787 to 845 in the sense orientation. This polynucleotide and others used were synthesized by Operon Technologies, Inc. The capture polynucleotide had an amine modification on its 5' terminus to facilitate attachment to a glass surface. Two 15 base SNP probes were synthesized to cover the region from nucleotides 851 to 865 surrounding polymorphic site 858. The two probes were identical in sequence to the two known sense sequences in this region. The SNP probe with nucleotide G at site 858 was labeled with the cyanine dye Cy3 during synthesis while the SNP probe with nucleotide A was labeled with Cy5. Finally, a 59-mer target polynucleotide was synthesized that was antisense to the region from 807 to 865 and contained a C at site 858.

A second sandwich assay was designed to identify the T to C base substitution known to occur at site 448 of the ApoE gene. In this case, the capture polynucleotide was sense to the region from nucleotide 377 to 445. The SNP probes were sense to the region from nucleotide 441 to 455 with the Cy3 labeled probe containing a T at position 448 and the Cy5 probe containing a C. The sample 59-mer was antisense to the region from 397 to 455 and contained an A at site 448.

The capture polynucleotides were deposited onto glass slides in a microdrop format at a concentration of 50 micromolar in 3×SSC using high-speed robotics (M. Schena et al., *Science* 1995, 270, 467–470; D. Shalon et al., *Genome Res.* 1996, 6, 639–645; D. Shalon, Ph.D thesis, Stanford University, 1996). The glass was coated with silylating reagents and derivatized to bind the amine modification of the capture probes. The arrays were allowed to sit overnight before washing. Unbound material was washed from the surface by the following steps: a 1 minute wash in 0.2% sodium dodecyl sulfate (SDS), followed by two 1 minute washes in water. The surface was then capped by a casein block (2 g of casein in 1,000 ml of 1×PBS buffer) for 30 minutes at 60 degrees. The slides were then washed again: a 1 minute wash in 0.2% SDS followed by two 1 minute washes in water. The arrays were then ready for hybridization. The array was then hybridized with the sample 59-mers for both the 448 and 858 regions and the 2 different cyanine dye labeled probe pairs. The samples and SNP probes were at a concentration of 500 picomolar in 5×SSC, 0.2% SDS. A total volume of 9 microliters was hybridized under a 22×22 mm glass cover slip (Corning Glassworks) at 45 degrees for 16 hours. The array was then washed at 37 degrees, first in 1×SSC, 0.1% SDS for 10 minutes, followed by 0.1×SSC for 10 minutes. A confocal fluorescence scanner (D. Shalon, Ph.D thesis, Stanford University, 1996) was used to image the array by exciting at 542 nm for the Cy3 fluorophore and 643 for the Cy5 fluorophore.

Specific hybridization of the SNP probe was seen for both sites 448 and 858. In both cases, the intensity of the Cy3 signal was stronger than that of Cy5, showing that the expected hybridization was achieved and identifying that the samples contained a C at site 858 and an A at site 448. The example illustrates that the array-based sandwich assay approach can be used to simultaneously detect sequence polymorphisms.

Example 2
Multi-Gene Sandwich Assay

The sandwich assay consists of capture polynucleotides, the sample of interest, and a detection probe for the SNP of interest. The detection can be done for each of the genes singly, or in a multiplex fashion. For each gene, a 59-mer capture polynucleotide was designed to encompass a region to the 5' end of the SNP site of interest. This capture polynucleotide was in the sense orientation, and terminated approximately 8 bp before the SNP site. The capture polynucleotide had an amine modification on its 5' end to facilitate attachment to a glass surface. For each gene, two SNP detection probes ranging from 14–18 nucleotides in length were synthesized. These probes differed by one base, corresponding to the known sense sequences of the polymorphic site, and the polymorphism sites located in the center of these polynucleotides. These SNP probes were adjacent to the capture probes. Each probe pair was end-labeled on the 5' end with Cy3 and Cy5 fluorescent dyes respectively. The probe pairs for all the genes were designed to have melting temperatures of as close to 56 deg C. as possible.

Finally, the samples for the assay consisted of double-stranded PCR fragments which were approximately 300 bp in length. These PCR fragments were generated by using gene specific primers from DNA samples which were homozygous allele A, homozygous allele B, or heterozygous respectively at the SNP site of interest. These DNA samples, in turn, had been generated by primer-extension preamplification (PEP) PCR from genomic DNA (L. Zhang et al., *Proc. Natl. Acad. Sci. USA,* 1992, 89, 5847–5851; K. Xu et al., *Hum. Reprod,* 1993, 8, 2206–2210). The PCR fragments were column-purified before use.

The capture polynucleotides were deposited onto glass slides in a microdrop format at a concentration of 50 micromolar in 3×SSC using high-speed robotics (M. Schena et al., *Science* 1995, 270, 467–470; D. Shalon et al., *Genome Res.* 1996, 6, 639–645; D. Shalon, Ph.D thesis, Stanford University, 1996). The coated glass slides were a generous gift from Paul Lee, Incyte Pharmaceuticals. Unbound material was washed from the surface by the following steps: 1 min wash in 0.2% SDS, followed by two 1 min washes in water. The surface was then capped by a casein block (2 g of casein in 1000 mL 1×PBS buffer) for 30 min at 60 deg. The slides were then washed again: 1 min wash in 0.2% SDS, followed by two 1 min washes in $H_2O$. The arrays were then ready for hybridization.

The hybridization samples consisted of each of the 10 SNP probe pairs at a concentration of 500 picomolar each, and the PCR samples of interest at a final concentration of 1 ng/uL in 5×SSC, 0.2% SDS at pH 9. These samples were heated to 90 deg for 5 minutes to denature the PCR fragments, and then quick-cooled on ice for 1 min before hybridization. A total volume of 9 microliters was hybridized under a 22×22 mm glass cover slip at 37 degrees for 16 hours. The array was then washed at 25 degrees in 1×SSC, 0.1% SDS for 10 minutes, followed by 0.1×SSC for 10 minutes. A confocal fluorescence scanner was used to image the array by exciting at 542 nm for the Cy3 fluorophore and 643 nm for the Cy5 fluorophore. Specific signal and thus hybridization of the SNP probe can be seen for each of the genes. It is possible to discriminate between homozygous wild-type, homozygous mutant, and heterozygous samples respectively. The example illustrates that the array-based sandwich assay approach can be used to simultaneously detect sequence polymorphisms.

Example 3
Minor Groove Binder Sandwich Assay

A sandwich assay was designed to identify the A to G base substitution known to occur at site 858 of the ApoE gene. A 59-mer capture polynucleotide was synthesized to cover the region from nucleotides 787 to 845 in the sense orientation. The capture polynucleotide had an amine modification on its 5' end to facilitate attachment to a glass surface. Two 11 base SNP probes were synthesized to cover the region from nucleotides 855 to 865 surrounding polymorphic site 858. The two probes were identical in sequence to the two known sense sequences in this region. The SNP probe with nucleotide G at site 858 was labeled with Cy3 on the 5' terminus during synthesis while the SNP probe with nucleotide A was labeled with Cy5. In addition, the minor groove binder 1,2-dihydro(3H)-pyrrolo[3,2-e]indole-7-carboxylate ($CDPI_3$) was conjugated to the 3' end of the oligonucleotide. The synthesis of a similar labeled SNP probe is detailed in Example 4. Finally, a 59-mer target polynucleotide was synthesized that was anti-sense to the region from 807 to 865 and contained a C at site 858.

The capture polynucleotides were deposited onto glass slides in a microdrop format at a concentration of 50 micromolar in 3×SSC using high-speed robotics (M. Schena et al., *Science* 1995, 270, 467–470; D. Shalon et al., *Genome Res.* 1996, 6, 639–645; D. Shalon, Ph.D thesis, Stanford University, 1996). The coated glass slides were a generous gift from Paul Lee, Incyte Pharmaceuticals. The arrays were allowed to sit overnight before washing. Unbound material was washed from the surface by the following steps: 1 min wash in 0.2% SDS, followed by two 1 min washes in water. The surface was then capped by a casein block (2 g of casein in 1000 mL 1×PBS buffer) for 30 min at 60 deg. The slides were then washed again: 1 min wash in 0.2% SDS, followed by two 1 min washes in $H_2O$. The arrays were then ready for hybridization.

The array was then hybridized with the sample 59-mer and the Cy labeled probe pair. The samples and SNP probes were at a concentration of 500 picomolar in 5×SSC, 0.2% SDS. A total volume of 9 microliters was hybridized under a cover slip at 45 degrees for 16 hours. The array was then washed at 37 degrees in 1×SSC, 0.1% SDS for 10 minutes, followed by 0.1×SSC for 10 minutes. A confocal fluorescence scanner was used to image the array by exciting at 542 nm for the Cy3 fluorophore and 643 nm for the Cy5 fluorophore.

Specific hybridization of the SNP probe was seen for site 858. The intensity of the Cy3 signal was stronger than that of Cy5, showing that the expected hybridization was achieved and identifying that the samples contained a C at site 858. In addition, the ratio between the Cy3 and Cy5 signal was increased by at least 10 fold compared to with the 15mer oligonucleotide probes in Example 1. The example illustrates that oligonucleotides conjugated to minor groove binders can be used to enhance the sensitivity of detection in the array-based sandwich assay approach. Example 4. SNP Detection with a Universal Detector Set.

The synthesis and use of a universal detector set of oligonucleotides is described. This set of compositions has the following general structure:

3'-(MGB)-NNXNN-(Label)-5', where:

MGB=a minor groove binder such as $CDPI_3$,

N=an equimolar mixture of all four bases A, G, C and T,

X=a specified base, i.e. either of A, G, C or T; and

Label=a uniquely detectable label associated with one of the four bases of X, such as a fluorophore. In this example, four unique fluorophores are used to comprise this detector set. For example, aminoreactive Cyanine dyes are used (Amersham-Pharmacia). Thus, for example, Cy2 (green) is used for X=A; Cy3 (orange) is used for X=G; Cy5 (far red) is used for X=C; and Cy7 (near infrared) is used for X=T.

The chemical structure of $CDPI_3$ is shown below:

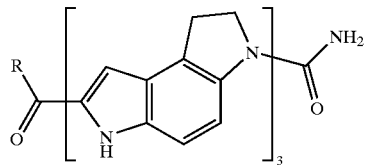

where R=a suitable linker for attachment to, in this case, the 3'-end of the oligonucleotide.

The preparation of $CDPI_3$-modified CPG (controlled pore glass support for solid phase oligonucleotide synthesis) is described by E. A. Lukhtanov et al., *Bioconjugate Chemistry*, 1995, 6, 418–426. Nucleotide phosphoramidite reagents are obtained from Glen Research (Sterling, Va., USA). Amino-Modifier C6 phosphoramidite reagent is also obtained from Glen Research. Each individual phosphoramidite reagent (A, G, C or T) is dissolved in dry acetonitrile to give a concentration of about 50 mM. To prepare a mixture for the random coupling steps (N), equal volumes from each solution are mixed together in one vial. All solution transfers are conducted using anhydrous techniques as are well known in the art. The appropriate phosphoramidite solutions (either of an individual base or a mixture of all four bases) are coupled onto the $CDPI_3$-modified CPG support using an Expedite™ Model 8905 Nucleic Acid Synthesis System (PerSeptive Biosystems, Framingham, Mass., USA). Synthesis is conducted sequentially from the 3'- to 5'-end according to protocols provided by the manufacturer. The Amino-Modifier C6 phosphoramidite reagent is coupled during the last synthesis cycle (i.e. at the 5'-end). Four separate syntheses are conducted in this manner: i.e. synthesis #1: X=A; synthesis #2: X=G; synthesis #3: X=C; synthesis #4: X=T. The amino-protecting group (monomethoxytrityl) is then removed from each synthesis column using an acidic detritylation protocol, as provided by the manufacturer.

Each of the four oligonucleotide syntheses are deprotected and cleaved from CPG support with 30% aqueous ammonium hydroxide at 55° C. for 6–12 h. The solution is decanted and evaporated to dryness using a Speed-Vac™ concentrator (Savant Corporation) to give the crude oligonucleotide products of the following sequence:

3'-(MGB)-NNXNN-(C6-aminolinker)-5' where:

X=A, G, C or T

Each of the four oligonucleotide compositions is then coupled to its respective Cyanine dye as follows. NHS-activated cyanine dye reagents (Cy2, Cy3, Cy5 or Cy7) are dissolved in dry dimethylsulfoxide to give a 10 mM solution. The oligonucleotide compositions (syntheses 1–4) are dissolved in 50 microliters of 0.1 M HEPES buffer (pH 8.0). Next, 25 microliters of the appropriate cyanine dye solution is added and the mixtures are reacted at 37° C. for 2 h. Then, 25 microliters additional cyanine dye solution is added and the reactions are continued at 37° C. for an additional 2–12 h. Unreacted dye is removed by size-exclusion chromatography using PD-10 cartridges as follows. First, the cartridges are equilibrated with five volumes of distilled, deionized water ($ddH_2O$). Next, the crude reaction mixtures are diluted with 0.4 mL $ddH_2O$ and applied to a cartridge. The cartridge is then eluted with 2×1.0 mL $ddH_2O$. Finally, the cartridge is eluted with 3.0 mL of $ddH_2O$ and the eluted product is collected and taken to dryness in a Speed-Vac™ concentrator.

The crude, dye-conjugated oligonucleotide compositions are then individually purified by reversed-phase HPLC using a Hewlett-Packard Model 1090 instrument (or equivalent), equipped with a diode-array UV detector. Column= Dynamax-300A analytical column (C-18, 4.6×250 mm, Rainin) (or equivalent). Elution is conducted using a linear gradient from 10% acetonitrile/0.1 M triethylammonium acetate (TEAA) to 50% acetonitrile/0.1 M TEAA. Peaks are monitored at 260 nm and also at a visible wavelength that is characteristic of each dye. Peaks having absorbance at both wavelengths are collected and evaporated to dryness to yield purified product.

At the conclusion of all HPLC purifications, the purified products are dissolved in a suitable hybridization buffer and their concentrations are determined by measuring the absorbance at 260 nm. The Universal Detector Set is then constructed by mixing equal concentrations of each of the four purified products to give a final working stock solution.

Figure 3:
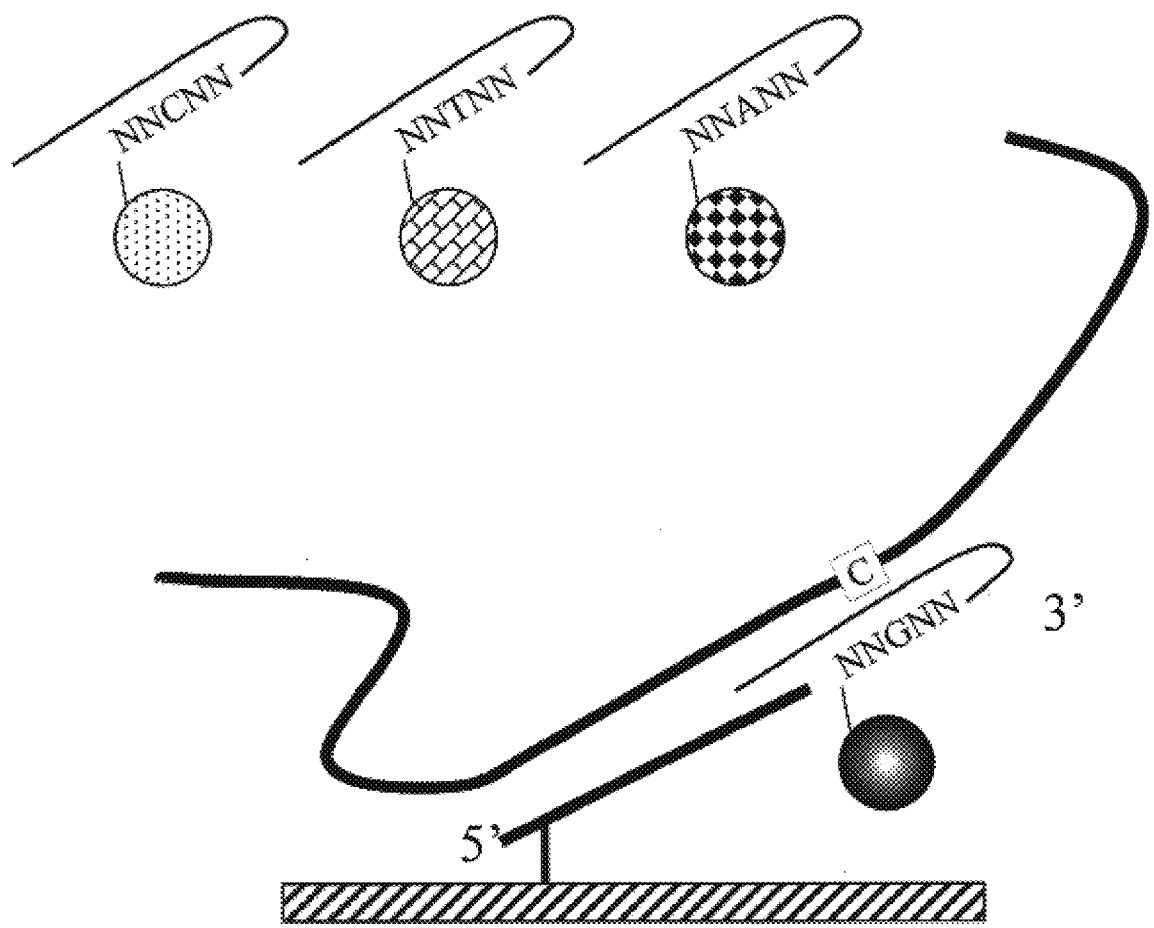
FIG. 3 shows a schematic of SNP detection using a support-bound capture polynucletide and a Universal Detector Set.

A schematic for the Universal Detector Set method is shown in FIG. 3. The capture polynucleotide is synthesized to be complementary to the target sample such that the end of the duplex formed between the capture polynucleotide and the sample polynucleotide is three bases away from the sequence polymorphism. An array of different capture polynucleotides is prepared for a multiple site assay. The sample polynucleotides and the universal detector set described above are mixed in the presence of this array. The sample polynucleotides sort onto the array of capture polynucleotides. Each sample becomes labeled by a single molecular species that is present in the universal detector set. This is ensured by the overlap of the minor groove binding conjugate and stacking interactions. The stringency conditions are chosen such that the detector molecules only hybridize to the sample if they are stabilized by stacking interactions with the end of the capture polynucleotide and overlap of the minor groove binder into the minor groove of the sample and capture polynucleotides. Since each molecule in the detector set is labeled to uniquely identify the $3^{rd}$ base in the molecule and the $3^{rd}$ base of the detector probe is constrained to hybridize to the $3^{rd}$ base of the sample from the end of the duplex formed between the sample and capture polynucleotides (the assayed site), the array element is thus labeled according to the assayed site. If a mixture of sample polynucleotides is present such that they differ at the assayed site, the array element is labeled with multiple detector probes with differentially detectable labels.

It is understood that, should the target polynucleotide extend in both directions beyond the region of hybridization to the capture polynucleotide, then it is possible for the same or separate species comprised within the Universal Detector Set to hybridize to both regions immediately adjacent to the capture polynucleotide. In this case, the hybridization of a species from the Universal Detector Set to the non-SNP-containing region will generate a separate signal that must be accounted for during data processing. Alternatively, this is remedied using either of the following modifications to the method:

Modification A. A modified capture polynucleotide is employed that contains 2'-O-methyl ribonucleotides (about 3–5) within the terminus that is opposite from the terminus that is directed toward the SNP-containing region of the target. 2'-O-methyl nucleoside phosphoramidites are purchased from Glen Research (Sterling, Va, USA). These are coupled into the capture polynucleotide using an automated nucleic acid synthesizer as described above, except that the coupling cycle for 2'-O-methyl nucleoside phosphoramidites is increased to about 10 minutes. The presence of 2'-O-methyl ribonucleotides prevents the MGB from binding to the hybrid formed between the capture polynucleotide and the target. Thus, species comprised within the Universal Detector Set cannot form stable duplexes within regions of the target other than the SNP-containing region.

Modification B. The target is designed such that the hybrid formed with the capture polynucleotide is blunt-ended at the end that is opposite from the SNP-containing region. In the case of the two ApoE polymorphisms site 858 A to G and site 448 T to C, the assay is constructed with a capture probe for samples generated around the 858 gene region that is complementary to the sample from bases 796 to 855. A second capture probe is constructed to capture samples generated around the 448 gene region that is complementary to the sample from bases 386 to 445. Samples which are generated from the specific gene regions are hybridized to the array in the presence of the universal detector set. Signal for universal detectors with A, G or both will be seen at the 858 region capture site depending on whether the sample is homozygous A, homozygous G or heterozygous. Similarly, signal for universal detector for T, C or both will be seen at the 448 region capture site.

Example 5. SNP Detection Using a Capture Polynucleotide Containing a Tethered MGB The synthesis and use of a capture polynucleotide containing a tethered MGB is described. This composition has the following generalized sequence:

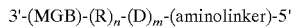

where

MGB=a minor groove binder such as CDPI$_3$ (see Example 4);

R=a 2'-O-methyl modified ribonucleotide;

D=a 2'-deoxyribonucleotide;

n=an integer, preferably about 5–10, such that the MGB is not capable of undergoing a binding interaction with a hybrid formed between the capture polynucleotide and a target polynucleotide, unless a SNP probe comprising 2'-deoxynucleotides is also present and hybridized to the capture polynucleotide at a region that is that is located within the vicinity of the MGB. The MGB described herewith does not bind to a heteroduplex formed between a target polynucleotide and a segment of capture polynucleotide comprising 2'-O-methyl modified ribonucleotides. However, the MGB is capable of binding to the duplex formed between the target polynucleotide and a SNP probe comprising 2'-deoxyribonucleotides, provided that said duplex is located a short distance away (i.e. about 0–3 bases) from the heteroduplex formed between the capture polynucleotide and the target polynucleotide; and m=a second integer defining the length of additional bases comprised within the capture polynucleotide that are needed for target immobilization, as defined within the body of this invention.

CDPI$_3$-modified CPG is described in Example 4. 2'-deoxyribo- and 2'-O-methylribonucleotide phosphoramidite reagents and Amino-Modifier C6 phosphoramidite reagent are obtained from Glen Research (Sterling, Va., USA). Oligonucleotide synthesis is conducted as described in Example 4, except that the coupling time for 2'-O-methylribonucleotide phosphoramidite reagents is increased to about 10 minutes. Deprotection of the crude oligonucleotide is likewise conducted as described in Example 4. Purification of the oligonucleotide is performed by reversed-phase HPLC using a Hewlett-Packard Model 1090 instrument (or equivalent), equipped with a diode-array UV detector. Column=Dynamax-300A analytical column (C-18, 4.6×250 mm, Rainin) (or equivalent). Elution is conducted using a linear gradient from 10% acetonitrile/0.1 M triethylammonium acetate (TEAA) to 50% acetonitrile/0.1 M TEAA. The product peak is assumed to elute with a longer retention time compared to shorter failure sequences. The purity of the recovered product is demonstrated by polyacrylamide gel electrophoresis. Bands are visualized by staining with an aqueous solution of Basic Blue dye (Sigma). The integrity of the oligonucleotide-MGB conjugate is demonstrated by comparison to samples of the same oligonucleotide sequence without MGB, and also by base composition analyses, using methods that are well known in the art.

Figure 4:
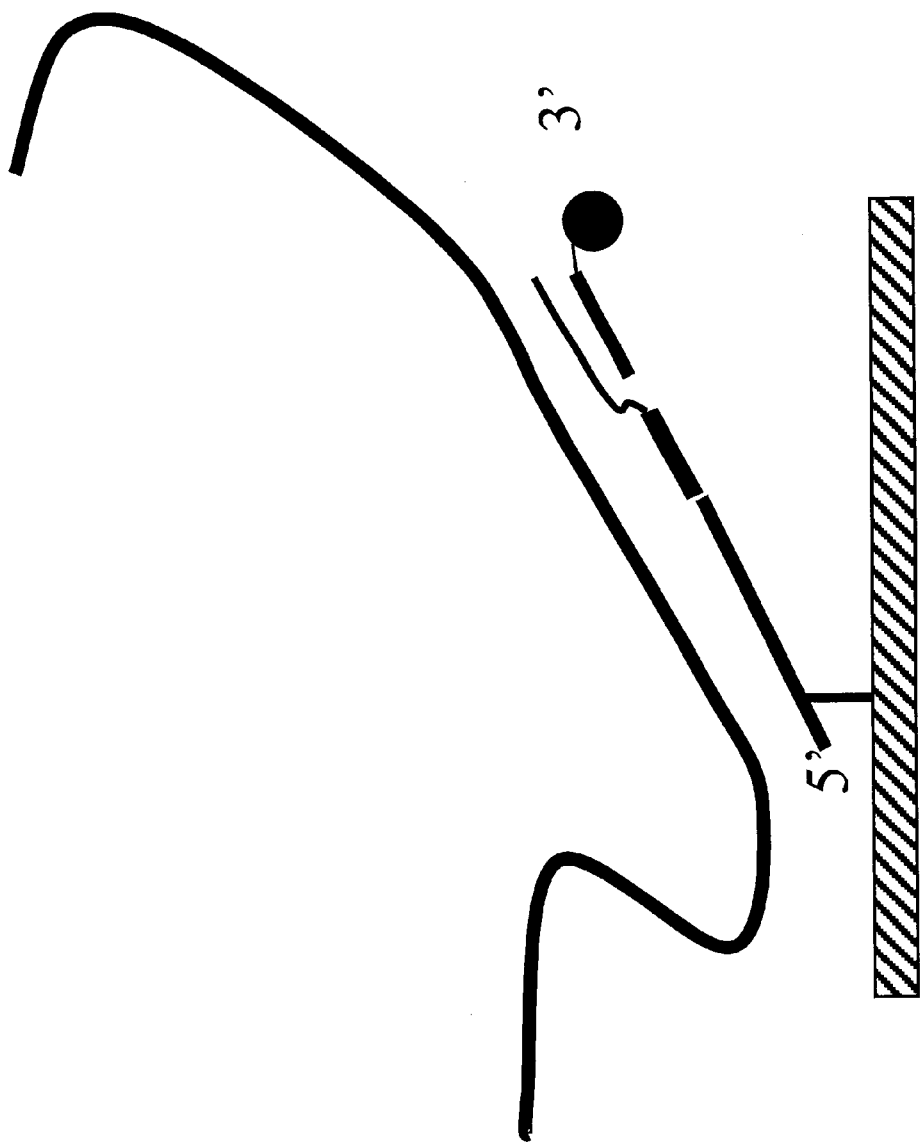
FIG. 4 shows a schematic of SNP detection using a chimeric support-bound capture polynucleotide containing a region of 2'-O-methyl ribonucleotides at one end and further tethered to an MGB.

The detection of polymorphisms in samples using the capture probe with MGB is done with either allele specific or universal detectors. A schematic for SNP detection according to this format is shown in FIG. 4. In the case of allele specific detectors, allele specific SNP probes are prepared with unique labels as in Example 1. The samples and SNP probes are hybridized with the array. Sample molecules will sort onto their distinct capture probes. The SNP probes will then hybridize only they hybridize adjacent to the end of the capture probes and can be stabilized by the minor groove binders tethered thereon.

In the case of a universal detector set, a set of short random oligos is made such that a single base is present at a particular site and is associated with a unique label. For example, the 3$^{rd}$ position of the oligos of the universal detector set is uniquely identified as A, C, G or T by appropriate labeling. The capture probes in this case are designed to hybridize the sample polynucleotide such that the assayed site is 3 bases from the end of the duplex formed between the capture and sample polynucleotides. The sample and universal detector set are hybridized with the array of capture probes. Again, the samples sort themselves onto the array based on their capture regions. Detector probes then identify the content of the 3$^{rd}$ base from the end of the capture sequence.

All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A method for detecting multiple SNPs in a population of target polynucleotides in parallel, the method comprising the steps of:
    (a) combining sample polynucleotides; capture polynucleotides and SNP probes under conditions wherein:
        a subset of the sample polynucleotides are target polynucleotides, each comprising a different capture region and a different SNP region comprising a corresponding different SNP,
        the capture polynucleotides are immobilized and arrayed at corresponding discrete elements on a substrate and each capture polynucleotide comprises a sequence which specifically hybridizes to a corresponding different capture region,
        each SNP probe comprises a sequence complementary to a corresponding different SNP region,
        the target polynucleotides are immmobilized by hybridizing to the capture polynucleotides whereby each target polynucleotide is immobilized at a corresponding discrete element of the substrate to provide a first discrimination of the sample polynucleotides, and
        the relative affinity of each SNP probe for the corresponding SNP region is sufficient to provide selective hybridization of the SNP probe to the corresponding SNF region, whereby each SNP probe selectively hybridizes to the corresponding SNP region to provide a second discrimination of the sample polynucleotides; and
    (b) detecting the presence of each SNP probe on the substrate, wherein the presence of a given SNP probe at a given element indicates the presence of the corresponding SNP in the corresponding target polynucleotide.

2. The method of claim 1, wherein the SNP probes are a subset of assay probes and the assay probes comprise a degenerate set of all possible same-sized polynucleotides.

3. The method of claim 1, wherein the sample polynucleotides comprise fragmented genomic DNA.

4. The method of claim 1, wherein the capture polynucleotides are a subset of immobilized polynucleotides and the immobilized polynucleotides are a segregated and arrayed cDNA library.

5. The method of claim 1, wherein the capture polynucleotides are immobilized and arrayed at corresponding discrete elements in high density.

6. The method of claim 1, wherein each SNP probe comprises a label.

7. The method of claim 1, wherein the SNP probes are a subset of assay probes and the relative affinity of each SNP probe for the corresponding SNP region is increased to provide enhanced discrimination between the corresponding SNP region and regions of the target polynucleotide other than the corresponding SNP region.

8. The method of claim 7, wherein the relative affinity of each SNP probe for the corresponding SNP region is increased at least in part by a method comprising the step of including in the combining step a reagent which normalizes the melting temperatures of the assay probes.

9. The method of claim 7, wherein the relative affinity of each SNP probe for the corresponding SNP region is increased at least in part by the SNP probe interacting with the capture polynucleotide or an auxiliary probe hybridized to the corresponding target polynucleotide.

10. The method of claim 7, wherein the relative affinity of each SNP probe for the corresponding SNP region is increased at least in part by the SNP probe interacting with the capture polynucleotide or an auxiliary probe hybridized to the corresponding target polynucleotide through a minor groove binder tethered to at least one of the SNP probe, the capture polynucleotide and the auxiliary probe.

11. The method of claim 7, wherein the assay probes comprise a degenerate set of all possible same-sized polynucleotides.

12. The method of claim 7, wherein the sample polynucleotides comprise fragmented genomic DNA.

13. The method of claim 7, wherein the capture polynucleotides are a subset of immobilized polynucleotides and the immobilized polynucleotides are a segregated and arrayed cDNA library.

14. The method of claim 7, wherein the capture polynucleotides are immobilized and arrayed at corresponding discrete elements in high density.

15. The method of claim 7, wherein each SNP probe comprises a label.

16. A method for detecting multiple SNPs in a population of target polynucleotides in parallel, the method comprising the steps of:
    (a) combining populations of each of sample polynucleotides, immobilized polynucleotides and assay probe pairs, each assay probe pair comprising first and second assay probes, under conditions wherein:
        a subset of the sample polynucleotides are target polynucleotides, each comprising a different capture region and a different SNP region comprising a corresponding different SNP,
        a subset of the immobilized polynucleotides are capture polynucleotides which are immobilized and arrayed at corresponding discrete elements on a substrate and each capture polynucleotide comprises a sequence which specifically hybridizes to a corresponding different capture region,
        a subset of the assay probe pairs are SNP probe pairs, each comprising a first SNP probe comprising a sequence complementary to a corresponding different SNP region, and a second SNP probe comprising a sequence having a single base mismatch with the same corresponding SNP region;
        the target polynucleotides are immobilized by hybridizing to the capture polynucleotides whereby each target polynucleotide is immobilized at a corresponding discrete element of the substrate to provide a first discrimination of the sample polynucleotides; and
        the relative affinity of each first SNP probe for the corresponding SNP region is increased at least in part by at least one of (a) a method comprising the step of including in the combining step a reagent which normalizes the melting temperatures of the assay probes and (b) the SNP probe interacting with the capture polynucleotide or an auxiliary probe hybridized to the corresponding target polynucleotide, sufficiently to provide selective hybridization of the first SNP probe to the corresponding SNP region to provide a second discrimination of the sample polynucleotides, whereby the ratio of hybridization of each first SNP probe to the corresponding SNP region to the hybridization of each second SNP probe to the same corresponding SNP region increases as a result of said conditions at least 2-fold; and (b) detecting the presence of each SNP probe on the substrate, wherein the presence of a given SNP probe at a given element indicates the presence of the corresponding SNP in the corresponding target polynucleotide.

17. The method of claim 10, wherein the assay probes comprise a degenerate set of all possible same-sized polynucleotides.

18. The method of claim 10, wherein the sample polynucleotides comprise fragmented genomic DNA.

19. The method of claim 10, wherein the capture polynucleotides are a subset of immobilized polynucleotides and the immobilized polynucleotides are a segregated and arrayed cDNA library.

20. The method of claim 10, wherein the capture polynucleotides are immobilized and arrayed at corresponding discrete elements in high density.

* * * * *

UNITED STATES PATENT AND TRADEMARK OFFICE
CERTIFICATE OF CORRECTION

PATENT NO. : 6,410,231 B1
DATED : June 25, 2002
INVENTOR(S) : Arnold et al.

It is certified that error appears in the above-identified patent and that said Letters Patent is hereby corrected as shown below:

Column 15,
Line 36, change "SNF" to -- SNP --.

Signed and Sealed this

Fourth Day of February, 2003

JAMES E. ROGAN
*Director of the United States Patent and Trademark Office*